United States Patent [19]
Krepski et al.

[11] Patent Number: 5,157,108
[45] Date of Patent: Oct. 20, 1992

[54] THERMALLY SENSITIVE LINKAGES

[75] Inventors: Larry R. Krepski; Steven M. Heilmann; Dean M. Moren; Jerald K. Rasmussen, all of St. Paul, Minn.

[73] Assignee: Minnesota Mining and Manufacturing Company, St. Paul, Minn.

[21] Appl. No.: 449,719

[22] Filed: Dec. 12, 1989

[51] Int. Cl.$^5$ .................... C08F 8/48; C07D 413/12
[52] U.S. Cl. .................... 528/503; 528/481; 525/326.8; 525/353; 525/379; 525/382; 544/71; 544/97; 548/216; 548/228
[58] Field of Search ............... 528/481, 503; 525/279, 525/326.8, 353, 379, 382; 548/228, 216, 228

[56] References Cited

U.S. PATENT DOCUMENTS

| | | | |
|---|---|---|---|
| 3,396,030 | 8/1968 | Haas | 96/114 |
| 3,488,327 | 1/1970 | Kollinsky et al. | 260/78.3 |
| 3,713,834 | 1/1973 | Fitzgerald | 96/114 |
| 3,721,565 | 3/1973 | Fitzgerald | 96/114 |
| 4,304,705 | 12/1981 | Heilmann et al. | 260/30.4 |
| 4,378,411 | 3/1983 | Heilmann et al. | 428/500 |
| 4,451,619 | 5/1984 | Heilmann et al. | 525/379 |
| 4,485,236 | 11/1984 | Rasmussen et al. | 544/69 |
| 4,539,383 | 8/1985 | Taylor | 526/304 |
| 4,639,286 | 1/1987 | Rasmussen et al. | 156/307.3 |
| 4,699,843 | 10/1987 | Charbonneau et al. | 428/355 |
| 4,737,560 | 4/1988 | Heilmann et al. | 526/304 |
| 4,785,070 | 11/1988 | Rasmussen et al. | 528/73 |
| 4,816,554 | 3/1989 | Katritzksy et al. | 528/210 |
| 4,852,969 | 8/1989 | Babirad et al. | 350/96.34 |
| 4,871,824 | 10/1989 | Heilmann et al. | 526/304 |

FOREIGN PATENT DOCUMENTS 1770454  10/1971  Fed. Rep. of Germany .

OTHER PUBLICATIONS

Iwakura et al., ". . . Preparation of Pseudoxazolones", Tetrahedron, vol. 23, 3363-73 (1967).
C. S. Cleaver, et al., *J. Am. Chem. Soc.*, 77, 1541 (1955).
M. Ueda et al., *J. Polymer Sci.*, Polymer Chem. Ed., 16, 155 (1978).
P. P. Policastro et al., *J. Polymer Sci., Polymer Chem. Part A*, 25, 2819 (1987).
"Polyazlactones", *Encyclopedia of Polymer Science and Engineering*, vol. 11, 2nd Ed., 1988, pp. 558-571.

*Primary Examiner*—Fred Teskin
*Attorney, Agent, or Firm*—Gary L. Griswold; Walter N. Kirn; Lorraine R. Sherman

[57] ABSTRACT

Compounds containing alpha-amidoacetyle linkages are described that are thermally labile and yield nucleophilic and azlactone products. Nucleophiles are useful as curing agents for epoxy resin sealants and adhesives and azlactones are useful in crosslinking systems for polymers.

27 Claims, 3 Drawing Sheets

THERMALLY SENSITIVE LINKAGES

FIELD OF THE INVENTION

This invention relates to a method of providing useful products from certain alpha-amidoacetyl compounds upon heating. The process causes liberation of two potentially useful azlactone and nucleophilic products. Azlactone products find utility, for example, in crosslinking systems for polymers, while released nucleophilic products find utility, for example, as initiating agents for the polymerization of epoxy resin adhesives and sealants.

BACKGROUND OF THE INVENTION

Azlactones (also referred to as 5(4H)-oxazolones or 2-oxazolin-5-ones) have been known for over 100 years and have been intensely investigated as valuable synthetic intermediates. An important and characteristic reaction of azlactones is a ring-opening addition reaction of various nucleophiles, HXR, in the equation (1) below (wherein X=O, S, NH, or NR and R means independent selections of alkyl and/or aryl groups), to provide the corresponding alpha-amidoacetyl derivative.

These nucleophilic addition reactions of azlactones have been utilized to prepare a wide variety of alpha-amidoacetic acids and derivatives including esters, amides, and thiolesters.

The facility with which azlactones undergo ring opening reactions with various nucleophiles has also been exploited in polymer chemistry. Reactions of bisazlactones with diamines, diols, and aminoalcohols have been used to prepare polyamides and polyesteramides (see, for example: C. S. Cleaver and B. C. Pratt, *J. Am. Chem. Soc.*, 77, 1541 (1955); M. Ueda, K. Kino, K. Yamaki, and Y. Imai, *J. Polymer Sci., Polymer Chem. Ed.*, 16, 155 (1978); P. P. Policastro and P. K. Hernandez, *J. Polymer Sci., Polymer Chem. Part A*, 25, 2819 (1987)). Certain of these polyamides derived from the reactions of bisazlactones may be transformed into novel polyimidazolinones by dehydration upon heating (U.S. Pat. No. 4,785,070). Other heterocycle-containing polymers, namely polyamidomethylbenzazoles, are prepared by the reaction of bisazlactones with bis(ortho-substituted aromatic amines) (see U.S. Pat. No. 4,816,554).

2-Alkenyl azlactones have also found broad utility in polymer science, and our recent review entitled "Polyazlactones" (contained in the *Encyclopedia of Polymer Science and Engineering*, Volume 11, 2nd edition, 1988, pp. 558–571) is incorporated herein by reference. Reaction of 2-alkenyl azlactones with appropriate nucleophiles, as depicted in the general equation above, leads to acrylamide-functional monomers which can be converted into polymers by standard free radical polymerization techniques. Several applications for these polymers in the photographic industry have been described, for example as binders for photographic emulsions to replace a portion of the gelatin typically used in photosensitive silver halide emulsions (U.S. Pat. No. 3,396,030; U.S. Pat. No. 3,713,834; and U.S. Pat. No. 3,721,565) or as base cleavable mordants for improved film processing (U.S. Pat. No. 4,539,383).

Alternative to reaction of 2-alkenyl azlactones with nucleophiles followed by polymerization of the resulting acrylamide-functional monomer is a procedure in which the 2-alkenyl azlactones themselves are homopolymerized or copolymerized with other monomers employing standard free radical polymerization conditions. The resulting azlactone-containing polymers derive significant utility from the presence of the pendant, reactive azlactone group as a site for polymer modification. A method of changing the hydrophilic/hydrophobic character of the azlactone-containing polymer by reaction with appropriate nucleophiles has been described (see U.S. Pat. No. 4,451,619). U.S. Pat. Nos. 4,304,705 and 4,378,411 also teach reaction of azlactone-functional polymers with nucleophiles such as 2-hydroxyethyl methacrylate providing polymers with pendant acrylic functionality. These polymers crosslink upon exposure to actinic radiation via the acrylic sites and become insoluble and are thus useful in the graphic arts. Utilization of pendant azlactone rings of alkenyl azlactone copolymers as reactive sites for crosslinking by reaction with diols or diamines for use in coating compositions has been described (see U.S. Pat. Nos. 3,488,327 and 4,699,843). Azlactone-functional polymer beads useful for attachment of complexing agents, catalysts, or biological materials such as enzymes or other proteins have been described (U.S. Pat. Nos. 4,737,560 and 4,871,824). Reaction of pendant azlactone groups of other 2-alkenyl azlactone copolymers with surface silanol groups on glass provides strongly adherent claddings for optical fibers (see U.S. Pat. No. 4,852,969).

In addition to incorporation of useful azlactone functionality into polymers by copolymerization of 2-alkenyl azlactones, certain amine- and mercaptan-functional oligomers and polymers can be rendered azlactone-functional by a different method, namely by Michael-type addition reactions of the amine or mercaptan groups of the oligomers and polymers to the carbon-carbon double bond of 2-alkenyl azlactones. The resultant azlactone-functional materials are useful for the preparation of polyamides (see U.S. Pat. Nos. 4,485,236 and 4,639,286).

SUMMARY OF THE INVENTION

Briefly, the present invention provides a method of providing useful azlactone and/or nucleophilic products by heating alpha-amidoacetyl and beta-amidopropionyl compounds. The method involves the steps of:

i) providing a compound comprising an alpha-amidoacetyl or beta-amidopropionyl structural linkage; and ii) heating said compound to effect release of azlactone and nucleophilic materials.

In this application:

"alkenyl" and "alkenylene" means the monovalent and polyvalent residues remaining after removal of one and at least two hydrogen atoms, respectively, from an alkene containing 2 to 16 carbon atoms;

"alkyl" and "alkylene" means the monovalent and polyvalent residues remaining after removal of one and at least two hydrogen atoms, respectively, from a linear or branched chain hydrocarbon having 1 to 14 carbon atoms;

"aryl" and "arylene" mean the monovalent and polyvalent residues remaining after removal of one and at least two hydrogen atoms, respectively, from an aromatic compound (single ring and multi- and fused-cyclic) having 5 to 12 ring atoms and includes substituted aromatics such as lower alkaryl and aralkyl, lower alkoxy, N,N-di(lower alkyl)amino, nitro, cyano, and lower alkyl carboxylic ester, wherein "lower" means C-1 to C-4;

"azlactone" means 2-oxazolin-5-one groups of Formula I and 2-oxazin-6-one groups of Formula II;

"alpha-amidoacetyl" means both acetyl linkages which are derivatives of five-membered azlactone rings as in Formula III and, for purposes of convenience unless otherwise specified, beta-amidopropionyl linkages which are derivatives of six-membered azlactone rings as in Formula IV;

"compound" has the traditional means of "a substance whose molecules consist of unlike elements and whose constituents cannot be separated by physical means", the meaning being further extended to include both thermoplastic and thermoset polymeric substances;

"cycloalkyl" and "cycloalkylene" mean the monovalent and polyvalent residues remaining after removal of one and at least two hydrogen atoms, respectively, from a cyclic hydrocarbon having 3 to 12 carbon atoms;

"lower alkyl" means C-1 to C-4 alkyl;

"substantially perfluorinated" means hydrocarbon groups in which at least 50 percent, preferably 85 percent, and more preferably 100 percent, or the hydrogen atoms have been replaced by fluorine;

"thermally labile" means that a material undergoes a retrograde reaction yielding azlactone and nucleophilic products at temperatures <250° C.

Several comprehensive reviews of azlactone chemistry have appeared such as the one by Y. S. Rao and R. Filler entitled "Oxazolones", contained in "Heterocyclic Compounds", Vol. 45 edited by I. J. Turchi, John Wiley and Sons, Inc.: New York, 1986, pp. 361-729.

During the long history of intensive investigation of azlactone materials and their derived nucleophilic addition products, including compounds containing alpha-amidoacetyl linkages of the invention, there has been no documentation nor even any speculation that some of these alpha-amidoacetyl linkages might be thermally reversible. Surprisingly, it has now been found that certain alpha-amidoacetyl compounds are indeed thermally labile and produce an azlactone compound and a nucleophile upon heating. This method is formally a retrograde of the reaction depicted in the equation (1) above and can be through of as a blocking or protecting of the azlactone and/or nucleophile by formation of the thermally labile alpha-amidoacetyl reaction product.

DESCRIPTION OF THE DRAWING

Further understanding of the invention in terms of determining effective retrograde temperatures and products obtained in the process can be achieved by examination of the accompanying drawing.

The Drawing shows a series of infrared (IR) spectra recorded at various temperatures of a layer comprising an alpha-amidoacetyl compound of the invention (Example 1). Although other techniques such as differential scanning calorimetry (DSC) and gas chromatography may be employed, we have found that infrared spectroscopy at elevated temperatures provides the most complete picture of the thermally initiated events that are taking place with the particular alpha-amidoacetyl compound. Beginning at 22° C. (FIG. 1), the aromatic ester absorption band at about 1750 cm$^{-1}$ is noted. At 120° C. (FIG. 2), the azlactone carbonyl absorption band at about 1820 cm$^{-1}$ appears at the expense of the aromatic ester carbonyl band. This transformation is more apparent at 140° C. (FIG. 3), and the retrograde reaction proceeds quite rapidly as the temperature increases, achieving conversions of approximately 40% at 160° C. (FIG. 4), 60% at 180° C. (FIG. 5), and 80% at 200° C. (FIG. 6).

DETAILED DESCRIPTION OF THE PREFERRED EMBODIMENTS

The present invention involves a process of providing a thermally labile alpha-amidoacetyl compound and heating to provide an azlactone product and a nucleophilic product. The alpha-amidoacetyl compounds of the invention have the general Formula V, which upon heating provide azlactone product VI and nucleophilic product HA according to the following reaction:

-continued wherein
p is the valence of G and can have any positive integral value from 1 to infinity;
m can have any positive integral value from 1 to
G can be alkyl, alkenyl, aryl, cycloalkyl, or polymeric monovalent terminal groups, i.e. when m=p=1, with number average molecular weights from 15, when G is methyl, to several million (such as 5 million or more) when G is a soluble, thermoplastic polymer group and, finally, to infinity when G is an insoluble, thermoset polymer group; or G can be alkylene, alkenylene, arylene, cycloalkylene, or polymeric polyvalent linking groups, i.e., when p is at least 2, with molecular weights from 14, when G is methylene, and ultimately to infinity when G is a thermoset polymeric group; or G can be a single (i.e., carbon-to-carbon) covalent bond; G can contain one or more of S, non-peroxidic O, N, P, S, Br, Cl, F, and Si atoms; and functional groups that can be included in G are one or more of alkyl, alkenyl, aryl, amide, ester, nitrile, nitro, sulfide, sulfoxide, sulfone, disulfide, azide, isothiocyanate, amine, hydroxyl, mercaptan, ether, urethane, quaternary ammonium and phosphonium, halogen, silyl, silyloxy, and the like, wherein the functional groups requiring substituents are substituted with hydrogen or alkyl or aryl groups where appropriate;

$R^1$ and $R^2$ independently represent an alkyl group of 1 to 14 carbon atoms, a cycloalkyl group of 3 to 12 carbon atoms, an aryl group of 5 to 12 ring atoms, or $R^1$ and $R^2$ taken together with the carbon atoms to which they are joined form a carbocyclic ring of 4 to 12 ring atoms;

$R^3$ and $R^4$ are independently hydrogen or lower alkyl;

n is 0 or 1;

A is selected from the group consisting of
—$SR^5$—$R^6$, wherein $R^5$ can be alkylene containing 1 to 14 carbon atoms or arylene containing 5 to 12 ring atoms, and $R^6$ can be hydrogen or G;
—OH;
—O—Ar—$R^6$, wherein Ar is arylene of 5 to 12 ring atoms, wherein $R^6$ is as defined above;
—$OCHR^7R_FR^8$, wherein $R^7$ can be hydrogen or $R_F$, wherein $R_F$ is a substantially perfluorinated alkylene or cycloalkylene group having from 2 to 14 carbon atoms, and $R^8$ can be hydrogen, fluorine, or G (defined above); or $R^7$ and $R_F$ together with the carbon atom to which they are joined form a ring of 4 to 12 ring atoms;
—N—($R^1$)—$R^5$—$R^6$;
—N=C($NR^1R^2$)$R^5R^6$;

—N=C($NR^1R^2$)—N($R^9$)$R^5R^6$; and wherein $R^1$, $R^2$, $R^5$, and $R^6$ are as defined above, or $R^1$, $R^2$, and $R^6$ together with the atoms to which they are joined form a ring of 4 to 12 ring atoms; and $R^9$ can be alkyl, cycloalkyl, or aryl.

The alpha-amidoacetyl compounds of Formula V are formally the nucleophilic addition reaction products of a nucleophile HA (wherein A is as defined above) and, an azlactone of Formula VI is equivalent to (wherein G, $R^1$, $R^2$, $R^3$, $R^4$, p and n are as defined above.)

Representative azlactone compounds of Formula VI of the invention may be any soluble or insoluble, low or high molecular weight compound that contains at least one azlactone group. Representative azlactone compounds include:

1) Low molecular weight (up to 1000 number average molecular weight), soluble azlactones include monoazlactones such as 2-alkenyl, 2-alkyl, and 2-aryl substituted azlactones and polyazlactones of the type disclosed in U.S. Pat. No. 4,485,236 (incorporated herein by reference) as well as those reported in the general literature such as those reported by S. M. Heilmann, et al., J. Polymer Sci.: Polymer Chem. Ed., 24, 1 (1986), also incorporated by reference. Useful low molecular weight, soluble azlactones include 2-vinyl-4,4-dimethylazlactone, 2-isopropenyl-4,4-dimethylazlactone, 2-vinyl-4,4-dimethyl-2-oxazin-6-one, 2,4-dimethyl-4-ethylazlactone, 2-dodecyl-4,4-dimethylazlactone, 2-phenyl-4,4-dimethylazlactone, 1,4-bis(4,4-dimethyl-2-oxazolin-5-one-2-yl)butane, 1,5-bis[(4,4-dimethyl-2- oxazolin-5-one-2-yl)ethylthio]-3-oxapentane, 2,2'-m-phenylenebis(4,4-dimethylazlactone), 2,2'-p-phenylenebis(4,4-dimethylazlactone), and the like.

2) High molecular weight (in the range of 1,000 to 5 million number average molecular weight), soluble azlactone compounds include free radical addition homopolymers and copolymers of 2-alkenyl azlactones such as those disclosed in U.S. Pat. No. 4,304,705, which is incorporated herein by reference. Examples of useful comonomers include styrene, ethyl acrylate, methyl methacrylate, n-butyl methacrylate, 1,1-dihydroperfluorooctyl methacrylate, octadecyl acrylate, iso-octyl acrylate, vinyl chloride, vinyl acetate, and the like.

3) Insoluble azlactone compounds possessing essentially an infinite molecular weight include those 2-alkenyl azlactone copolymers with the aforementioned mono(ethylenically unsaturated) comonomers and at least one multi(ethylenically unsaturated) comonomer, whose copolymerization results in the joining of polymer chains causing crosslinking and insolublization. Suitable multi(ethylenically unsaturated) comonomers include but are not limited to those disclosed in U.S. Pat. Nos. 4,379,201 and 4,871,824, also incorporated herein by reference. Useful insoluble azlactones include a reverse phase suspension polymerization copolymer comprising 2-vinyl-4,4-dimethylazlactone and methylenebisacrylamide and a dispersion polymerization copolymer comprising 2-vinyl-4,4-dimethylazlactone and trimethylolpropane trimethacrylate.

Representative HA compounds of the invention include any soluble or insoluble, low or high molecular weight compound that contains at least one nucleophilic group (wherein $R^1$, $R^2$, $R^5$, $R^6$, $R^7$, $R^8$, $R^9$, and $R_F$ are as defined above) selected from the group consisting of:

i) Thiols, $HSR^5R^6$

Useful soluble, low molecular weight thiols include dodecyl mercaptan, thiophenol, 2-mercaptoethyl ether, and pentaerythritol tetrathioglycolate. Useful soluble, high molecular weight thiols include polyethylene glycol di(2-mercaptoacetate), LP ™ -3resins supplied by Morton Thiokol Inc. (Trenton, N.J.), and Permapol ™ P3 resins supplied by Products Research & Chemical Corp. (Glendale, Calif.). Useful insoluble thiol compounds include the soluble, high molecular weight thiols previously mentioned that have been crosslinked by a variety of techniques such as ionizing radiation and retain thiol functional groups. Another useful insoluble thiol compound is the reaction product of chloromethylated copoly(styrene-divinylbenzene) and thiourea disclosed by Frechet, et al., *Polymer*, 20, 675 (1979), incorporated herein by reference.

ii) Water, HOH iii) Phenols, $HO-Ar-R^6$

Useful soluble low molecular weight phenols include phenol, p-methoxyphenol, p-phenylazophenol, p-nitrophenol, and 8-hydroxyquinoline. Useful soluble, high molecular weight phenols include poly(p-hydroxystyrene) and resole and novalac resins, prior to final cure. After cure these latter crosslinked phenol-formaldehyde polymers are useful insoluble phenol compounds. Another useful insoluble phenol compound is the reaction product of lithiated copoly(styrene-divinylbenzene) and oxygen also disclosed by Frechet, et al., ibid.

iv) Substantially perfluorinated alcohols, $HOCHR^7R_FR^8$

Useful perfluorinated alcohols include 2,2,2-trifluoroethanol; 1H,1H-heptafluoro-1-butanol; undecafluorocyclohexylmethanol; perfluorocyclohexanol; 1H,1H,7H-dodecafluoro-1-heptanol; 1H,1H-pentadecafluorooctanol-01; 1H,1H,11H-eicosafluoro-1-undecanol; and others disclosed in U.S. Ser. No. 07/267,035, which is incorporated herein by reference.

v) Secondary Amines, $HN(R^1)R^5R^6$

Useful secondary amines include diethylamine, N-methylaniline, piperidine, morpholine, and polymers prepared using N-isopropylaminopropyl methacrylamide.

vi) Amidines, $HN=C-(NR^1R^2)-R^5R^6$ and $$HNR^1C=NR^2 \\ | \\ R^5R^6$$

Useful amidine compounds are benzamidine and 2-methylimidazoline.

vii) Guanidines, $HN=C-(NR^1R^2)-N(R^9)R^5R^6$ and

$$HNR^1-C=NR^2 \\ | \\ N(R^9)R^5R^6$$

Examples of useful guanidine compound are tetramethylguanidine, and 1,5,7-Triazabicyclo[4.4.0]dec-5-ene (available from Fluka Chemical Corp., Ronkonkoma, N.Y.), and N,N'-dicyclohexyl-4-morpholinecarboxamidine (available from Aldrich Chemical Co., Milwaukee, Wis.)

The alpha-amidoacetyl compounds of Formula V are prepared most easily by mixing the nucleophile HA and the azlactone of Formula VI, either in the presence or absence of a solvent and optionally in the presence of a catalyst. Whether this reaction occurs in a reasonable amount of time, e.g., <24 hours, is largely determined by the nucleophile (HA), the presence of a catalyst, the reaction temperature, and the concentration of the reactants. The most reactive HA nucleophiles of the invention are the guanidines and amidines, and they generally require no catalyst for efficient addition to azlactone compounds at room temperature. Reactions of secondary amines and water generally proceed at reasonable rates in the presence of Bronsted acidic catalysts such as trifluoroacetic acid, p-toluenesulfonic acid, and ethanesulfonic acid, employed in concentrations of from 0.1 to 10 mole percent (based on reactant). Thiols, phenols, and substantially perfluroinated alcohols generally add efficiently in the presence of cyclic amidine bases such as 1,8-diazabicyclo[5.4.0]undec-7-ene (DBU) and 1,5-diazabicyclo[4.3.0]non-5-ene (DBN), both available from Aldrich Chemical Co., Milwaukee, Wis., employed in the same concentrations as the acidic catalysts. When the addition reaction is slow at room temperature (about 22° C.), elevating the temperature increases reaction rate; useful temperatures are from 22°-80° C. If solvents are employed, they should not react with either the nucleophile or the azlactone, and suitable organic solvents include ethyl acetate, methyl ethyl ketone, toluene, chloroform, dichloromethane, and tetrahydrofuran. Furthermore, the amount of solvent employed should be as small as possible because dilution of reactants slows reaction rate. Useful amounts of solvent employed are from 0.9 to 0.1, preferably 0.7 to 0.1, and most preferably 0.5 to 0.1 weight fraction of the reaction solution. Progress of the reaction is conveniently monitored by observing the disappearance of the strong and characteristic azlactone carbonyl absorption band in the infrared at about 5.5 microns (about 1800 cm$^{-1}$).

Alternative to reaction of a nucleophile with a polymeric azlactone as a route to either the soluble or insoluble, high molecular weight alpha-amidoacetyl compounds of the invention, a nucleophile may be reacted with a 2-alkenyl azlactone to produce an N-acryloyl alpha-amidoacetyl compound of Formula VII

VII (wherein $R^{10}$ can be hydrogen or methyl and $R^1$, $R^2$, $R^3$, $R^4$, n, and A are as defined above.) The N-acryloyl-alpha-amidoacetyl compounds of Formula VII may then be homopolymerized or copolymerized with other vinyl monomers employing standard free radical polymerization conditions.

Although alpha-amidoacetyl compounds of the invention are most easily prepared by the nucleophile-azlactone reactions described above, it is also contemplated as within the scope of the invention to provide the alpha-amidoacetyl compounds by conventional condensations of nucleophiles with alpha-amidoacids of Formula VIII

VIII (wherein G, $R^1$, $R^2$, $R^3$, $R^4$, and n are as defined above.) In these reactions standard condensation reagents such as dicyclohexylcarbodiimide or ethyl chloroformate may be employed. In these cases, the end product of the condensation reaction is the alpha-amidoacetyl compound of Formula V, although a transient intermediate azlactone of Formula VI, may actually be formed.

Having provided the alpha-amidoacetyl compounds of the invention in step one, step two of the invention involves heating the compounds to effect the reversion or retrograde reaction to form the azlactone product of Formula VI and the HA nucleophilic product. The method of heating depends in large measure upon the particular application and physical form of the alpha-amidoacetyl compound of Formula V. Heating may be applied to the bulk sample or to a solution of the alpha-amidoacetyl compound, either in the presence or absence of a catalyst. Suitable solvents include those solvents useful in the preparation of the Formula V compounds as well as others that are relatively high boiling organic solvents such as xylene, ethylbenzene, tetralin, decalin, chlorobenzene, anisole, glyme solvents, and the Isopar solvents available from Exxon Chemical Co. (Houston, Tex.). Reaction temperatures necessary to effect the desired retrograde reaction depend on the particular alpha-amidoacetyl compound linkage and the presence of catalysts. Catalysts and amounts employed are essentially the same as those useful for the preparation of the alpha-amidoacetyl compounds from azlactone and nucleophilic reactants, i.e., Bronsted acids and cyclic amidine bases, preferably in an amount from 0.1 to 10 mole percent, although increased quantities of catalysts of up to 20 mole percent may be useful to lower the temperature required for effective generation of the desired azlactone and/or nucleophilic products. Generally, in order to achieve adequate shelf stability (of alpha-amidoacetyl compounds) it is desirable that temperatures in excess of about 80° C. be required to bring about effective retrograde reaction rates. However, it is also desirable because of the tendency of most organic materials to undergo undesirable thermal decomposition that the temperature required for retrograde reaction not exceed about 250° C. Heating may be applied more or less uniformly to the alpha-amidoacetyl compounds of the invention by use of conventional ovens or by application or infrared and microwave radiation. It is also contemplated as being within the scope of the invention that, especially with coatings and films of the alpha-amidoacetyl compounds, heat may be applied more or less non-uniformly by methods known in the art such as focussed laser and infrared radiation or by use of thermal printing heads.

The utility of the thermally labile alpha-amidoacetyl compounds of the present invention derives from their ability to function as blocked or protected azlactone and nucleophilic compounds. Upon application of an efficacious amount of heat, the azlactone and nucleophilic compounds become available, and either or both of the compounds may be utilized to accomplish a specific purpose. The utility of the invention is manifold and limited only by the imagination of the practioner. Two specific examples of utility are given in the examples below. One example utilizes the azlactone product as part of a thermally reversible crosslinking system; such systems have broad appeal to the polymer technologist in melt-processable, high strength materials. The other utility example shows use of the thermally created nucleophilic product; in this case a strong nucleophile is generated which is capable of initiating an epoxy-azlactone polymerization/crosslinking reaction.

Objects and advantages of this invention are further illustrated by the following examples, but the particular materials and amounts thereof recited in these examples, as well as other conditions and details, should not be construed to unduly limit the invention. In all cases Ph=phenyl Me=methyl, Et=ethyl, Bu=butyl, and pTs=para-toluenesulfonyl.

EXAMPLE 1

This example teaches that an alpha-amidoacetyl aromatic ester, i.e., the reaction product of an azlactone and a phenol, is thermally labile.

Preparation of the Alpha-Amidoacetyl Compound

Poly(2-vinyl-4,4-dimethylazlactone) [p(VDM)] was prepared in ethyl acetate solution according to a procedure in U.S. Pat. No. 4,304,705 (column 16; lines 45-64). To 10.63 grams of the homopolymer solution, which contained 4.40 grams (0.0317 mole) of polymer, were added 3.93 grams (0.0317 mole) of p-methoxyphenol, 13.21 grams of ethyl acetate, and 0.12 gram (0.0008 mole) of 1,8-diazabicyclo[5.4.0]undec-7-ene (DBU). The reaction that ensued was mildly exothermic and was completed within 30 minutes as evidence by the disappearance of the azlactone carbonyl absorption band in the infrared spectrum. The resulting polymer possessed a weight-average molecular weight as determined by gel permeation chromatography in tetrahydrofuran solution of 2.23 million. The polymer displayed a glass transition temperature as measured by differential scanning calorimetry (DSC) of 87° C.

Examination of Thermal Activity

Figure 1:
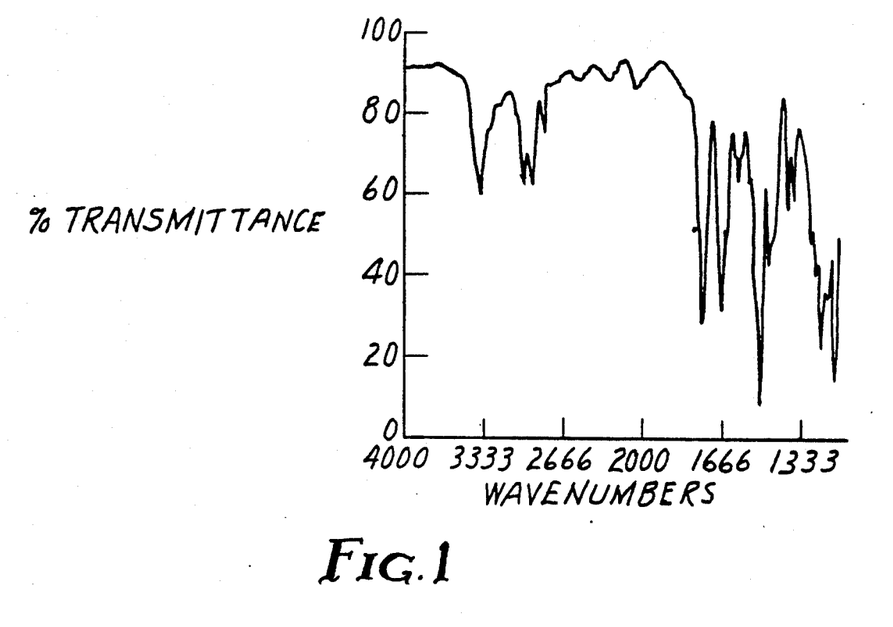
Figure 2:
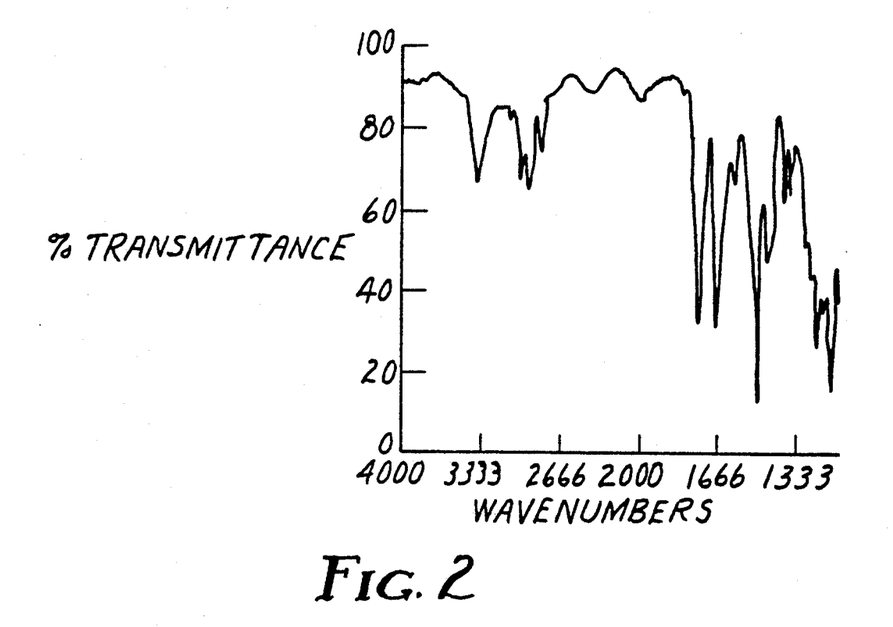
Figure 3:
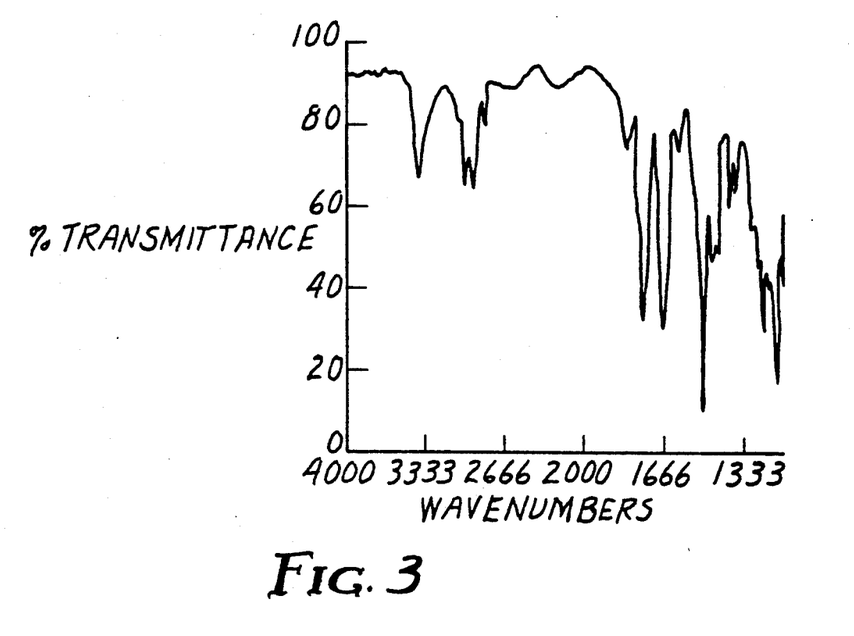
Figure 4:
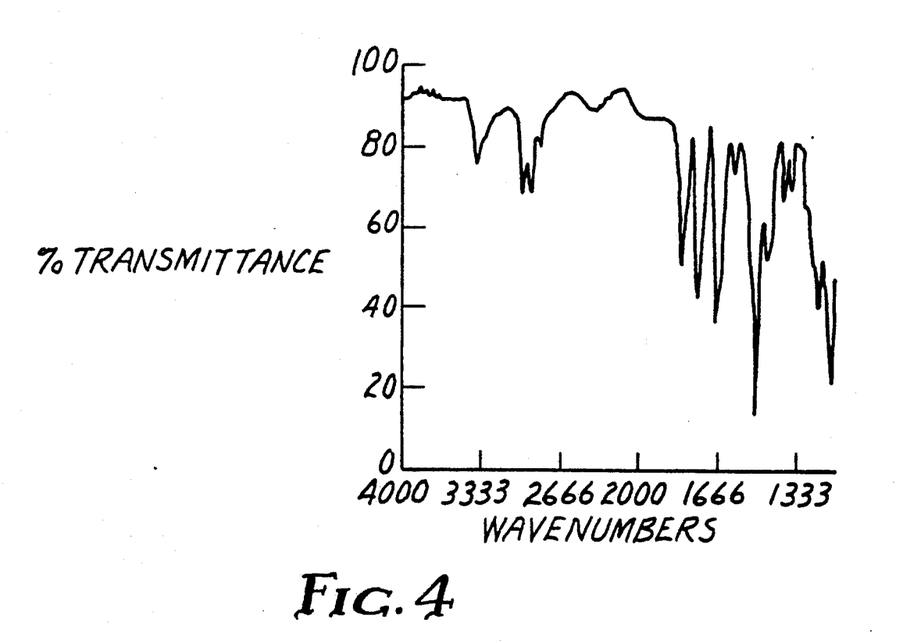
Figure 5:
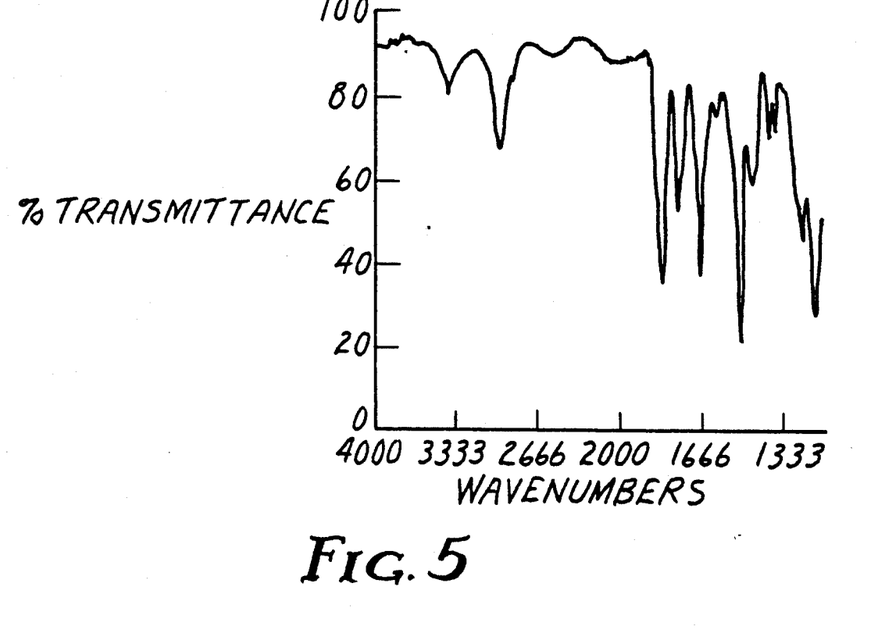
Figure 6:
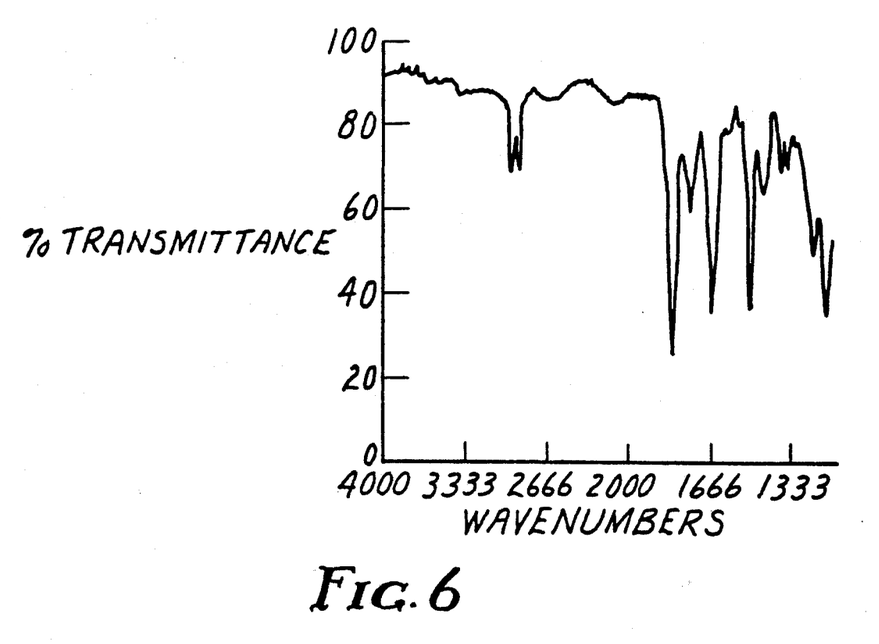

A small portion of the above alpha-amidoacetyl compound solution was coated onto a salt plate, and the ethyl acetate solvent was allowed to evaporate leaving a clear, amorphous film of the polymer. Infrared spectra were obtained using a Nicolet 7199 FTIR employing a Celli Omega Programmable Infrared Cell (Series CN-2010). The procedure involved incrementally increasing the temperature of the cell 20° C. within two minutes, and the infrared spectrum was subsequently recorded after an additional five minutes at the respective temperature. Relevant infrared spectra are shown in FIGS. 1 through 6. It is apparent that the desired retrograde reaction forming p(VDM) and p-methoxyphenol begins at about 120° C.

EXAMPLES 2-14

Similarly prepared as in Example 1 were the alpha-amidoacetyl compounds prepared from p(VDM) and the various nucleophiles in Table 1. Onset temperatures are indicated for the retrograde reactions determined using the infrared technique. These examples illustrate the breadth of thermally labile alpha-amidoacetyl compounds of the invention, as well as the influence of certain catalysts such as p-toluenesulfonic acid (Example 10 compared to Example 9).

TABLE 1

Nucleophiles Providing Thermally Labile Alpha-Amidoacetyl Linkages

| EXAMPLE | Nucleophile | Retrograde Onset Temperature |
|---|---|---|
| 2 | $C_6H_5OH$ | 140 |
| 3 | $p\text{-}O_2NC_6H_4OH$ | 150 |
| 4 | $p\text{-}PhN=NC_6H_4OH$ | 120 |
| 5 | $o\text{-}CH_3OC_6H_4OH$ | 140 |
| 6 | $CF_3CH_2OH$ | 150 |
| 7 | HOH | 220 |
| 8 | $Ph(Et)NH$ | 180 |
| 9 | $Et_2NH$ | 225 |
| 10 | $Et_2NH$ + 5% pTsOH | 180 |
| 11 | $n\text{-}C_{12}H_{25}SH$ | 180 |
| 12 | $C_6H_5SH$ | 150 |
| 13 | $HN=C(NMe_2)NMe_2$ | 180 |
| 14 | (N-methyl-piperazine, N, NH, $CH_3$) | 90 |

EXAMPLE 15

This example teaches that beta-amidopropionyl compounds derived from nucleophiles and six-membered ring azlactones (2-oxazin-6-ones) are thermally labile as well.

Preparation of Poly(2-Vinyl-4,4-dimethyl-2-oxazin-6-one)

The monomer was prepared using the procedure of Heilmann, et al., *J. Polymer Sci.: Polymer Chem, Ed.*, 22, 1179 (1984). A solution was prepared consisting of 2-vinyl-4,4-dimethyl-2-oxazin-6-one (20 grams), ethyl acetate (30 grams), and azobis(isobutyronitrile) (available from Eastman Kodak Co., Rochester, N.Y.) (0.10 gram). The solution was purged with carbon dioxide, sealed, and placed in an Atlas Launderometer (available from Atlas Electric Devices Co., Chicago, Ill.) at 55° C. for 24 hours. Upon visual inspection the polymerization had proceeded to such an extent that the polymer solution would barely flow at room temperature. Dilution with ethyl acetate (50 grams) provided a pourable, more handleable polymer solution whose polymer solids was 21.0 weight percent.

Preparation of the Beta-Amidopropionyl Aromatic Ester and Thermolysis

To 3.23 grams of the above polymer solution containing 0.68 gram (0.0044 mole) of polymer were added 0.42 gram (0.0044 mole) of phenol and 0.01 gram of DBU. The solution was allowed to stand at room temperature for 12 hours. IR analysis showed that the azlactone carbonyl absorption band had disappeared and been replaced by expected absorption bands of the beta-amidopropionyl aromatic ester compound.

A film of the polymer was examined using the thermal IR procedure of Example 1, and the onset temperature for the retrograde reaction was 160° C.

COMPARATIVE EXAMPLES 1-7

Also prepared by the method of Example 1 were the alpha-amidoacetyl compounds of p(VDM) and the various nucleophiles of Table 2. These linkages were determined to be thermally inactive below 250° C. using the infrared procedure.

TABLE 2

Nucleophiles Providing Thermally Inactive Alpha-Amidoacetyl Linkages

| COMPARATIVE EXAMPLE | Nucleophile |
|---|---|
| 1 | $NH_3$ |
| 2 | $n\text{-}BuNH_2$ |
| 3 | $n\text{-}BuOH$ |
| 4 | $PhNH_2$ |
| 5 | $CF_3(CF_2)_7CH_2CH_2OH$ |
| 6 | (cyclohexanone oxime, =NOH) |
| 7 | (succinimide-N-OH derivative) |

EXAMPLE 16

This example teaches utility of the alpha-amidoacetyl aromatic ester compounds of the invention as a reversible crosslinking system.

Preparation of a Bisacrylamide Crosslinking Monomer

3-Hydroxybenzyl alcohol (available from Aldrich Chemical Co., Milwaukee, Wis.) (1.33 grams; 0.0107 mole), 2-vinyl-4,4-dimethylazlactone (available from SNPE, Inc., Princeton, N.J.) (3.13 grams: 0.0225 mole), ethyl acetate (10 mL), and DBU (0.10 gram; 0.0007 mole) were mixed, and the solution was heated to 55° C. for 12 hours. A white crystalline solid precipitated and was collected by filtration. The solid weighed 4.15 grams (96% yield), and although it melted broadly from 50° to 60° C., its ¹H-NMR spectrum gave an excellent fit for the bis(alpha-amidoacetyl compound) shown below, which possesses one thermally labile linkage (A) and one thermally inactive linkage (B).

Preparation of a Crosslinked Polymer containing the Thermally Reversible Linkage and thermolysis Thereof

A solution was prepared consisting of methyl methacrylate (8.25 grams), the above bisacrylamide (1.75 grams), and Irgacure 651 photoinitiator (available from Ciba-Geigy Corp., Ardsley, N.Y.) (0.03 gram). The solution was poured into a shallow aluminum pan (55 mm diameter) and irradiated in a nitrogen atmosphere under a bank of four Blacklight bulbs (available from Sylvania GTE, Danvers, Mass.) for one hour. Similarly, a control sample consisting of methyl methacrylate and, instead of the bisacrylamide, decanediol dimethacrylate (available from Sartomer Co., West Chester, Pa.,) was prepared and irradiated. Both cured samples were hard disks approximately 3 mm thick, and both samples were insoluble in tetrahydrofuran and chloroform.

Small pieces (ca. 0.5 gram) of the cured polymers were placed between the plates of a 2 kilogram Williams Plasticity Tester (available from Precision Scientific Inc., Chicago, Ill.) container in an oven at 235° C. The spacing between the plates for the bisacrylamide crosslinked sample was initially 3.40 mm. After one hour, the spacing had decreased to 1.19 mm, and upon visual inspection of the sample, it was obvious that viscous flow had taken place. With the control sample, the heat and pressure caused shattering of the sample to a granular consistency which exhibited no flow. After the thermal treatment, again, both samples were insoluble in tetrahydrofuran and chloroform solvents.

EXAMPLE 17

This example teaches utility of the nucleophilic product of the thermally induced retrograde reaction of the alpha-amidoacetyl compounds of the invention. The example utilizes the alpha-amidoacetyl compound of Example 13 which releases a very strong nucleophile, tetramethylguanidine, in order to initiate an epoxy-azlactone polymerization.

To 4.35 grams of the solution polymer of Example 13 which container 1.30 grams of the poly(acylguanidide) were added 1.74 grams of bisphenol A diglycidyl ether (DER 331; available from Shell Chemical Co., New York, N.Y.) to provide a viscous solution. A small portion was poured into an aluminum cup and placed in an oven at 150° C. for one hour. The resulting cured polymer was hard and somewhat brittle; the material was insoluble in dichloromethane solvent. IR analysis showed an ester carbonyl absorption band was present that would be expected to result from the following polymerization-crosslinking reactions:

crosslinked polymer containing an ester group

We claim:

1. A method comprising the step of heating a composition consisting essentially of a compound having the formula:

wherein
G is an alkyl, alkenyl, aryl, or cycloalkyl, or monovalent terminal group having a number average molecular weight in the range of 15 to infinity; or an alkylene, alkenylene, arylene, cycloalkylene or polyvalent polymeric linking group having a number average molecular weight in the range of 14 to infinity; or a carbon-to-carbon covalent bond;
p is the valence of G and can have any positive integral value from 1 to infinity;
m can have any positive integral value from 1 to p;
$R^1$ and $R^2$ independently represent an alkyl group of 1 to 14 carbon atoms, a cycloalkyl group of 3 to 12 carbon atoms, an aryl group of 5 to 12 ring atoms, or $R^1$ and $R^2$ taken together with the carbon atom to which they are joined form a carbocyclic ring of 4 to 12 ring atoms;
$R^3$ and $R^4$ are independently hydrogen or lower alkyl;
n is 0 or 1;
A is selected from the group consisting of $-SR^5-R^6$, wherein $R^5$ can be alkylene or arylene containing 1 to 14 carbon atoms and 5 to 12 ring atoms, respectively, and $R^6$ can by hydrogen or G;
$-O-Ar-R^6$, wherein Ar is arylene of 5 to 12 ring atoms, wherein $R^6$ is as defined above;
$-OCHR^7R_FR^8$, wherein $R^7$ can be hydrogen or $R_F$, $R_F$ is a substantially perfluorinated alkylene or cycloalkylene group from 2 to 14 carbon atoms, and $R^8$ can be hydrogen, fluorine, or G (defined above); or substantially perfluorinated $R^7$ and $R_F$ together with the carbon atom to which they are joined form a carbocyclic ring of 4 to 12 ring atoms;
$-N-(R^1)-R^5-R^6$;
$-N=C(NR^1R^2)R^5R^6$;

$-N=C(NR^1R^2)-N(R^9)R^5R^6$; and wherein $R^1$, $R^2$, $R^5$, and $R^6$ are as defined above or $R^1$, $R^2$, and $R^6$ together with the atoms to which they are joined form a ring of 4 to 12 ring atoms, and $R^9$ can be alkyl, cycloalkyl, or aryl;
to provide an azlactone and a nucleophile HA, wherein A is as previously defined.

2. The method according to claim 1 wherein G further comprises one or more of S, non-peroxidic O, N, P, S, Br, Cl, F, and Si atoms.

3. The method according to claim 1 wherein G further comprises one or more functional groups selected from the group consisting of alkyl, alkenyl, aryl, amide, ester, nitrile, nitro, sulfide, sulfoxide, sulfone, disulfide, azide, isothiocyanate, amine, hydroxyl, mercaptan, ether, urethane, quaternary ammonium and phosphonium, halogen, silyl, and silyloxy.

4. The method according to claim 3 wherein said functional group is further substituted by at least one alkyl or aryl group.

5. The method according to claim 1 wherein said heating step takes place at a temperature less than 250° C.

6. The method according to claim 1 wherein said heating step takes place at a temperature in the range of 80° to 250° C.

7. The method according to claim 1 wherein said azlactone is a low molecular weight soluble monoazlactone.

8. The method according to claim 1 wherein said azlactone is a high molecular weight soluble azlactone homopolymer or copolymer.

9. The method according to claim 1 wherein said azlactone is an insoluble azlactone copolymer.

10. The method according to claim 1 wherein said nucleophile is a thiol having the formula $HSR^5R^6$, wherein $R^5$ and $R^6$ are as previously defined.

11. The method according to claim 1 wherein said nucleophile is a phenol having the formula $HO-Ar-R^6$, wherein Ar is an aromatic group having 5 to 12 ring atoms wherein the aromatic group can have a single ring or a multi or fused ring system, and $R^6$ is as previously defined.

12. The method according to claim 11 wherein said phenol is selected from the group consisting of 8-hydroxyquinoline, p-phenylazophenol, and p-methoxyphenol.

13. The method according to claim 1 wherein said nucleophile is a substantially perfluorinated alcohol.

14. The method according to claim 13 wherein said alcohol has the formula $HOCHR^7R_FR^8$ wherein $R^7$, $R^8$, and $R_F$ are as previously defined.

15. The method according to claim 13 wherein said alcohol is a 1,1-dihydroperfluorinated alcohol.

16. The method according to claim 1 wherein said nucleophile is a secondary amine having the formula $HN(R^1)R^5R^6$ wherein $R^1$, $R^5$ and $R^6$ are as previously defined.

17. The method according to claim 1 wherein said nucleophile is an amidine having the formula wherein $R^1$, $R^2$, $R^5$, $R^6$ are as previously defined.

18. The method according to claim 17 wherein said amidine is 2-methylimidazoline.

19. The method according to claim 1 wherein said nucleophile is an amidine having the formula $NH=C-(NR^1R^2)-R^5R^6$ wherein $R^1$, $R^2$, $R^5$ and $R^6$ are as previously defined.

20. The method according to claim 1 wherein said nucleophile is a guanidine having the formula $HN=C-(NR^1R^2)-N(R^9)R^5R^6$ wherein $R^1$, $R^2$, $R^5$, $R^6$ and $R^9$ are as previously defined.

21. The method according to claim 20 wherein said guanidine is tetramethylguanidine.

22. The method according to claim 1 wherein said nucleophile is a guanidine having the structure $$HNR^1-C=NR^2$$
$$|$$
$$N(R^9)R^5R^6$$

wherein $R^1$, $R^2$, $R^5$, $R^6$, and $R^9$ are as previously defined.

23. The method according to claim 20 wherein said quanidine is selected from the group consisting of 1,5,7-triazobicyclo[4.4.0]dec-5-ene and N,N'-dicyclohexyl-4-morpholinecarboxamidine.

24. The method according to claim 1, wherein in said formula V, n is zero.

25. The method according to claim 24 wherein said compound comprises units of the formula:

26. The method according to claim 1, wherein in said formula V, n is 1.

27. A method comprising a step of heating a composition consisting essentially of 1) a compound having the formula:

wherein

G is an alkyl, alkenyl, aryl, or cycloalkyl, or monovalent terminal group having a number average molecular weight in the range of 15 to infinity; or an alkylene, alkenylene, arylene, cycloalkylene or polyvalent polymeric linking group having a number average molecular weight in the range of 14 to infinity; or a carbon-to-carbon covalent bond;

p is the valence of G and can have any positive integral value from 1 to infinity;

m can have any positive integral value from 1 to p;

$R^1$ and $R^2$ independently represent an alkyl group of 1 to 14 carbon atoms, a cycloalkyl group of 3 to 12 carbon atoms, an aryl group of 5 to 12 ring atoms, or $R^1$ and $R^2$ taken together with the carbon atom to which they are joined form a carbocyclic ring of 4 to 12 ring atoms;

$R^3$ and $R^4$ are independently hydrogen or lower alkyl;

n is 0 or 1;

A is selected from the group consisting of —S—$R^5$—$R^6$, wherein $R^5$ can be alkylene or arylene containing 1 to 14 carbon atoms and 5 to 12 ring atoms, respectively, and $R^6$ can be hydrogen or G;

—O—Ar—$R^6$, wherein Ar is arylene of 5 to 12 ring atoms, wherein $R^6$ is as defined above;

—OCHR$^7$R$_F$R$^8$, wherein $R^7$ can be hydrogen or R$_F$, R$_F$ is a substantially perfluorinated alkylene or cycloalkylene group from 2 to 14 carbon atoms, and $R^8$ can be hydrogen, fluorine, or G (defined above); or substantially perfluorinated $R^7$ and R$_F$ together with the carbon atoms to which they are joined form a carbocyclic ring of 4 to 12 ring atoms;

—N—($R^1$)—$R^5$—$R^6$;

—N=C(NR$^1$R$^2$)R$^5$R$^6$;

$$-NR^1C=NR^2$$
$$|$$
$$R^5R^6$$

—N=C(NR$^1$R$^2$)—N(R$^9$)R$^5$R$^6$; and $$-NR^1C=NR^2$$
$$|$$
$$N(R^9)R^5R^6$$

wherein $R^1$, $R^2$, $R^5$, and $R^6$ are as defined above or $R^1$, $R^2$, and $R^6$ together with the atoms to which they are joined form a ring of 4 to 12 ring atoms, and $R^9$ can be alkyl, cycloalkyl, or aryl; and 2) at least one of a chemically effective amount of a catalyst and an organic solvent for the compound of formula V above;

to provide an azlactone and a nucleophile HA, wherein A is as previously defined.

* * * * *

UNITED STATES PATENT AND TRADEMARK OFFICE
CERTIFICATE OF CORRECTION

PATENT NO. : 5,157,108

DATED : October 20, 1992

INVENTOR(S) : Larry R. Krepski et al.

It is certified that error appears in the above-indentified patent and that said Letters Patent is hereby corrected as shown below:

On the cover sheet, in the Abstract, first line, "amidoacetyle" should read -- amidoacetyl --.

Col. 1, line 22, "X=O" should read -- X = 0 --.

Col. 5, line 24, "1 to" should read -- 1 to p; --.

Col. 6, lines 37-45, replace formula VI with the following:

Col. 10, line 15, "application or" should read -- application of --.

Col. 13, line 36, "container" should read -- contained --.

Col. 13, line 57, "container" should read -- contained --.

UNITED STATES PATENT AND TRADEMARK OFFICE
CERTIFICATE OF CORRECTION

PATENT NO. : 5,157,108

DATED : October 20, 1992

INVENTOR(S) : Larry R. Krepski et al.

It is certified that error appears in the above-indentified patent and that said Letters Patent is hereby corrected as shown below:

Col. 15, lines 30-31, "$-SR-^5-R^6$" should read -- $-SR^5-R^6$ --.

Col. 16, lines 26-27, "$HO-A-r-R^6$" should read -- $HO-Ar-R^6$ --.

Col. 18, lines 15-16, "$-SR-^5-R^6$" should read -- $SR^5-R^6$ --.

Signed and Sealed this

Twenty-ninth Day of November, 1994

Attest:

BRUCE LEHMAN

Attesting Officer

Commissioner of Patents and Trademarks